United States Patent [19]
Furlow et al.

[11] Patent Number: 5,254,104
[45] Date of Patent: Oct. 19, 1993

[54] DEVICE FOR PERICATHETER RETROGRADE

[75] Inventors: William L. Furlow, Nashville; L. Dean Knoll, Brentwood; Ralph C. Benson, Jr., Mt. Juliet, all of Tenn.; Russel R. Voght, Elk River, Minn.

[73] Assignee: Center for Urological Treatment & Research, Nashville, Tenn.

[21] Appl. No.: 781,748

[22] Filed: Oct. 22, 1991

[51] Int. Cl.[5] ............................................. A61M 5/00
[52] U.S. Cl. ................................... 604/264; 604/280
[58] Field of Search ................ 604/21, 27, 73, 76, 604/93, 96, 124, 181, 218, 264, 280, 283

[56] References Cited

U.S. PATENT DOCUMENTS 4,601,713 7/1896 Fuqua .................................. 604/280
4,966,148 10/1990 Millar ................................... 128/673

OTHER PUBLICATIONS

"Pericatheter Retrograde Urethrography Introduction of a New Device and Technique", Journal of Urology, vol. 142, pp. 1533-1535 (Dec. 1989).

Primary Examiner—C. Fred Rosenbaum
Assistant Examiner—Manuel Mendez
Attorney, Agent, or Firm—Daivd P. Gordon

[57] ABSTRACT

A pericatheter device is disclosed for enabling the introduction of contrast medium into the urethra and bladder neck of a patient with a catheter indwelling to enable radiographic visualization without removal of the catheter. The device has a crescent-shaped elongate member, a mating member for mating with a syringe, and a spacer member coupling the elongate member and mating member. A straight through-bore is provided from the mating member through the spacer member and through the elongate member so that a liquid contrast medium can be injected therethrough.

13 Claims, 3 Drawing Sheets

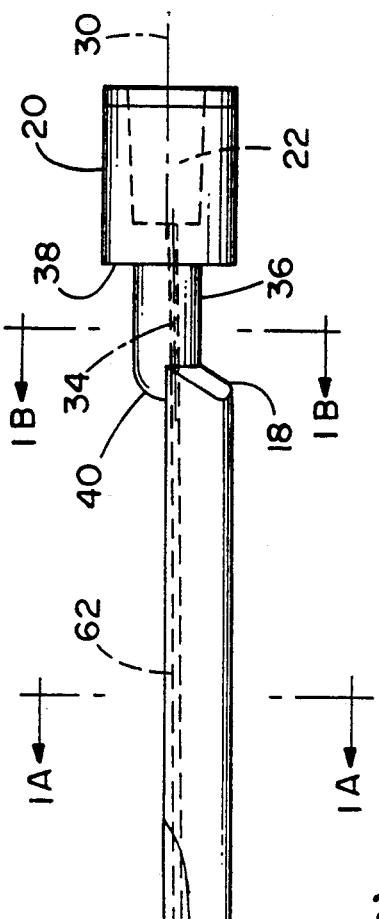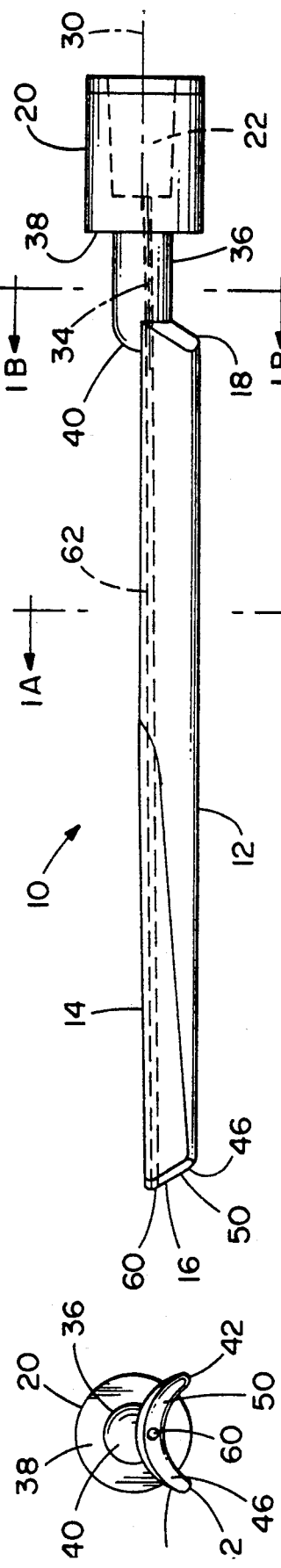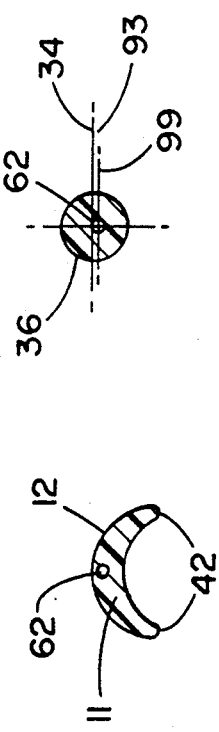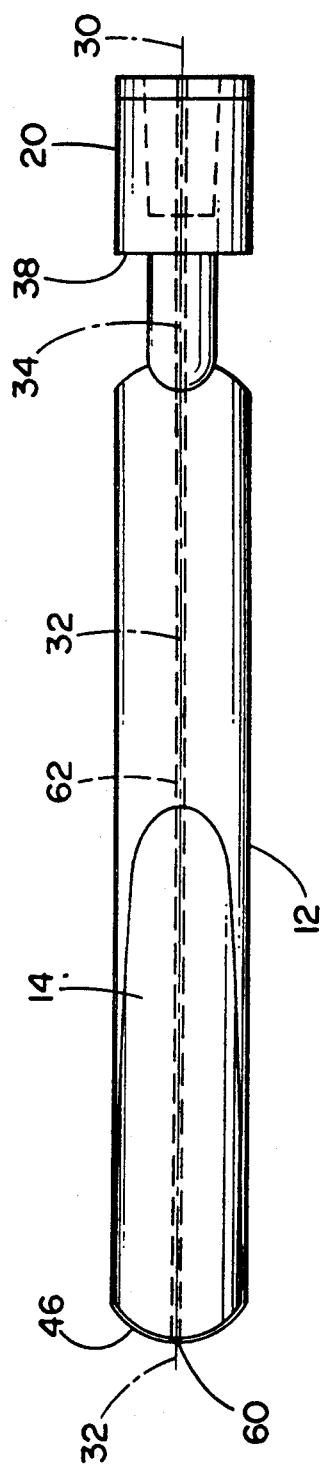

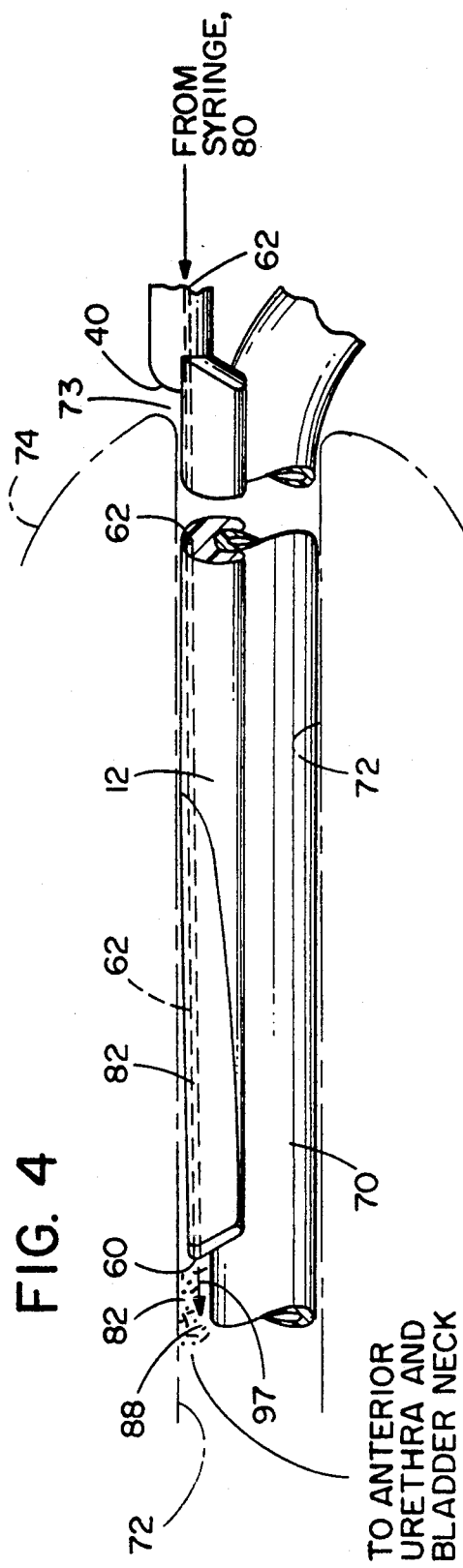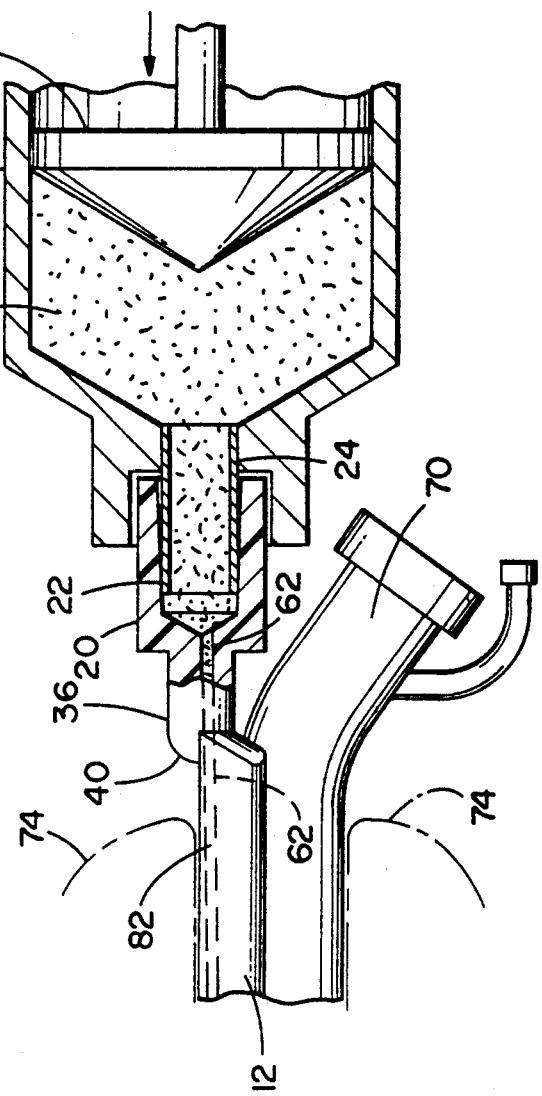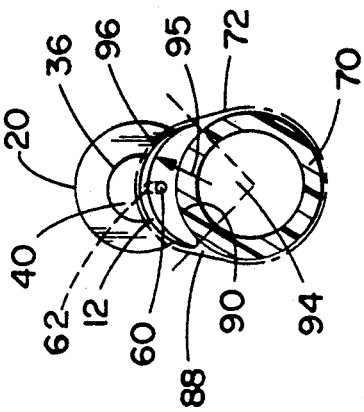

DEVICE FOR PERICATHETER RETROGRADE

BACKGROUND OF THE INVENTION

This invention relates to pericatheter devices for use in urethography. More particularly this invention relates to a disposable pericatheter type device for use in conjunction with urethrography techniques which involve the radiographic visualization of a patient's urethra and bladder neck.

A well known urological procedure involves the insertion of a catheter into the urethra of a patient in connection with radical retropubic prostatectomy or urethroplasty. Tests have been performed, as described by Knoll, Furlow and Karsburg in *The Journal of Urology*, Volume 142, December 1989, pages 1533–1535 using a device to inject, prior to removal of the catheter, a contrast medium through the urethra and around the catheter to reveal the urethra and all anastomotic sites studied using radiographic procedures. This device and technique avoids the need to routinely remove the catheter to evaluate the integrity of anastomosis after radical retropubic prostatectomy or urethroplasty and eliminates trauma to the anastomosis if re-catheterization is required.

While the procedures as described in the above-noted publication can be very effective, the device described therein for employment in the procedure is a metal, non-disposable type of device which has several drawbacks. First, because the device is metal and intended for reuse, the device requires regular sterilization. Second, because of the interior configuration of the device which has a fluid conduit with several bends therein, the fluid injected through the device can be subject to unwanted blockage.

SUMMARY OF THE INVENTION

It is an object of this invention to provide a disposable device for retrograde urethography with a catheter indwelling.

It is a further object of the invention to provide a device for retrograde urethrography with a catheter indwelling in which the possibility of obstruction of injected liquid contrast medium is eliminated.

It is another object of the invention to provide an easily manufactured unitary device for retrograde urethrography.

It is another object of this invention to provide a device which is easily inserted an appropriate distance into a urethra with a catheter indwelling.

The present invention relates to a pericatheter device which enables introduction of liquid contrast medium into the urethra of a patient with a catheter indwelling. The liquid contrast medium is provided to permit radiographic visualization of the urethra and bladder neck. The device of the invention therefore enables an evaluation of the state of healing following radical retropubic prostatectomy or urethroplasty without requiring removal of the catheter. Thus, the prospect of re-catheterization and associated trauma is avoided.

More particularly, the device of the present invention is a disposable device in the form of a unitary single component formed in one piece from rigid, smooth surfaced plastic. The device includes an elongate element of crescent-shaped cross-section tapering slightly toward its distal end; a luer slip or mating means which is spaced from the elongate element and which receptively engages an output of a syringe type device adapted to contain contrast medium; and a spacer member intermediate the elongate element and the mating member. The spacer member is substantially in line with the locking member and off-set with respect to the elongate element so that there is a step-shaped protuberance where the elongate element joins the spacer member. A relatively narrow but essentially straight through-bore is provided extending from an opening in the distal end of the elongate element through the spacer member and through the mating member. The through-bore is in fluid communication with the fluid outlet of the syringe. Thus, fluid flowing out of the syringe can flow through the pericatheter device of the invention and out of the opening in the distal end of the elongate member of the pericatheter device.

Additional objects and advantages of the invention will be apparent from the detailed description taken in conjunction with the drawings and claims.

BRIEF DESCRIPTION OF THE DRAWINGS

FIG. 1 is a side elevation view of the device of the present invention;

FIG. 1A is a cross-sectional view of FIG. 1 at line 1A—1A.

FIG. 1B is a cross-sectional view of FIG. 1 at line 1B—1B.

FIG. 1C is a partial front elevation view of the device of FIG. 1 in place over a catheter.

FIG. 2 is a top plan view of the device of FIG. 1;

FIG. 3 is a front elevation view of the device of FIG. 1;

FIG. 4 and FIG. 5 are partial side elevation views showing of the operation of the device of FIG. 1.

DETAILED DESCRIPTION OF THE PREFERRED EMBODIMENT

Figure 6:
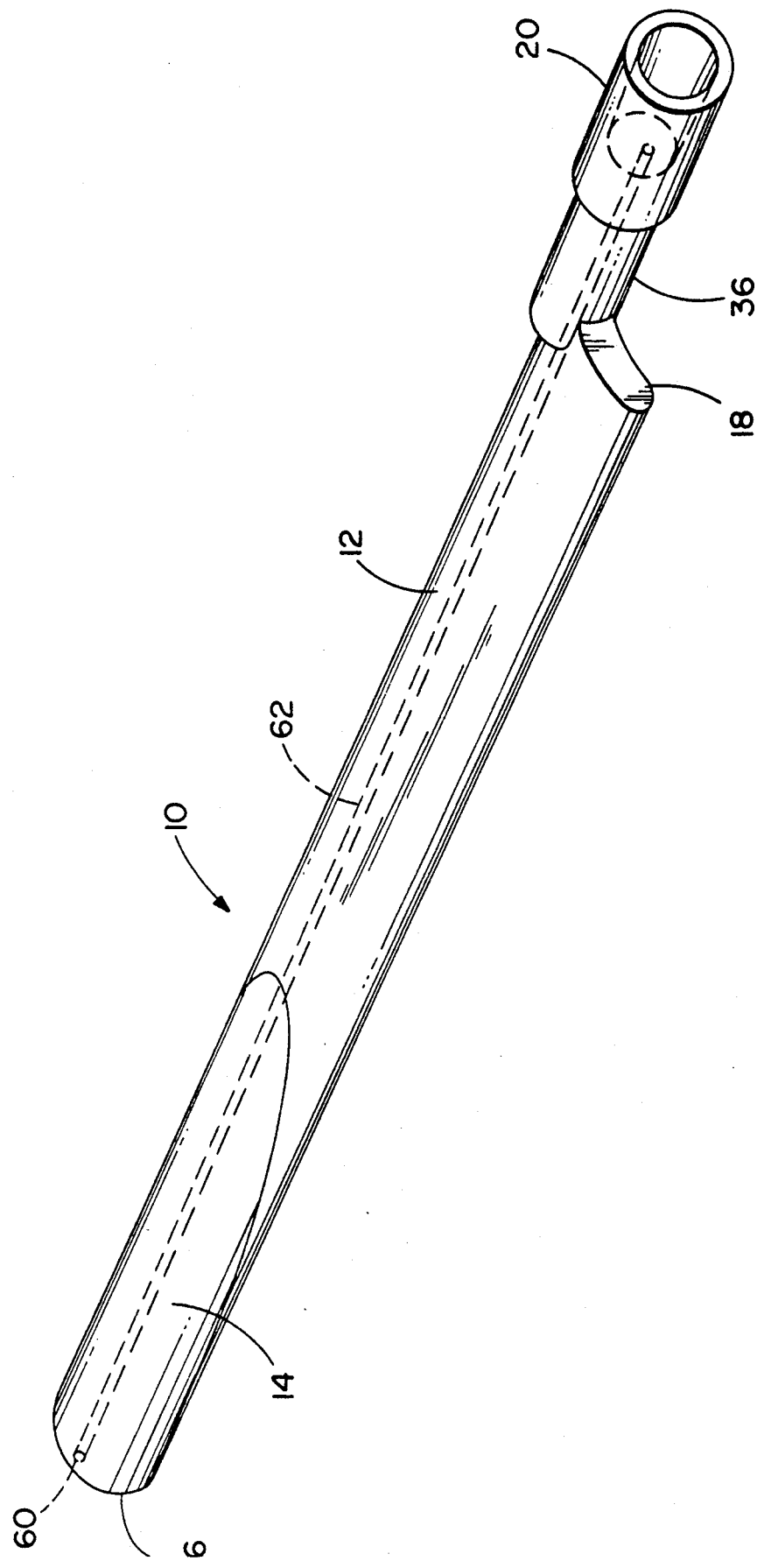
FIG. 6 is an isometric view of the device of FIG. 1.

Turning to FIGS. 1-3, a side elevation view, a top plan view, and a front elevation view are seen of a disposable pericatheter type device 10 for use in retrograde urethrography procedures with a catheter indwelling in accordance with the invention. The device 10 is preferably made from a rigid smooth surfaced plastic such as polypropylene in one unitary piece, e.g. by molding, and includes an elongate element 12, a spacer member 36, and a mating member 20. The preferred polypropylene is polypropylene Profax PD626, although other polypropylenes and other plastics can be utilized.

The elongate element 12 of device 10 preferably has a crescent shaped cross-section as shown at 11 in FIG. 1(A) which is shaped along its inner surface to extend around and slide over a catheter device. Elongate element 12 also has a slightly tapered portion 14, e.g. about 1° taper, which extends from the distal end 16 of elongate element 12 about 30% to 50% of the distance to the proximal end 18 of the elongate member. The taper facilitates movement of the device 10 into a patient's urethra (72 in FIG. 4).

The mating member 20 of device 10 is suitably configured as a well known female luer slip or female luer lock. As shown in FIGS. 1-3, the mating member 20 is a luer slip which is cylindrical in shape and has an aperture 22 for receptively engaging the male luer of a syringe-type device such as luer 24 of FIG. 5. The central axis 30 of mating member 20 is generally parallel to the longitudinal axis 32 of elongate element 12 and to the central axis 34 of spacer member 36.

The spacer member 36 is located intermediate elongate element 12 and mating member 20 and is integrally joined to both and unitary therewith. Spacer member 36 is preferably cylindrical in shape and of lesser cross-section diameter than mating member 20. The spacer member 36 is contiguous at one end with the mating member 20 at peripheral wall 38, and spacer member 36 is contiguous at its other end with elongate element 12. Spacer member 36, while preferably being essentially in-line and coaxial with mating member 20, is off-set from elongate element 12 to form a step-shaped protuberance 40 which can serve to limit the advancement of the device into urethra 72 as indicated at 73 in FIG. 4. The end of spacer member 36 which forms protuberance 40 is curved and is generally hemispherical in shape and is easily formed by conventional molding practices.

As best seen in FIGS. 1 and 3, elongate element 12 has beveled lateral edges 42 and distal edges 46 which flare back, as indicated at 50, toward the proximal end 18 of elongate element 12 to facilitate advancement of the device 10 alongside catheter tube 70. A substantially central aperture 60 is provided at the distal end of the elongate element 12. A straight through-bore 62 extends from aperture 60 through elongate element 12, spacer member 36 and mating member 20 to communicate with aperture 22 thereof which receptively engages the male luer of the syringe device as indicated at 24 of FIG. 5. Because through-bore 62 is straight, the possibility of blockage of the contrast medium is virtually eliminated. In addition, by providing a straight through-bore, conventional insert molding techniques can be used in manufacturing the pericatheter device 10, thereby keeping costs to a minimum.

In use, with reference to FIGS. 4 and 5, with catheter 70 indwelling in a urethra 72 and resiliently curved out of the axis of the urethra as shown (off-axis spacer member providing room for the same), the elongate element 12 of the pericatheter device 10 is gently inserted alongside catheter 70. The device 10 is then advanced along the catheter 70 until the step-shaped protuberance 40 reaches and is closely adjacent meatus 74 to restrain further advancement of the device 10. When in place as above-described, and with reference to FIG. 5, with mating member 20 receptively engaging at 22 the male luer 24 of syringe 80, the liquid contrast medium 82 which is contained in the syringe 80 can be injected. In particular, by movement of plunger 84, the liquid contrast medium 82 is caused to flow into through-bore 62 and pass straight through mating member 20, spacer means 36 and elongate element 12 and out of outlet aperture 60 into the urethra 72. The fluid is advanced under pressure in the narrow space 88 in the urethra alongside catheter 10 and into the bladder neck. In this manner, state of the art radiography techniques are enabled and may be employed to determine the extent of healing without requiring removal of the catheter 70. The flow of contrast medium 82 from outlet aperture 60 of elongate element 12 is slightly, downwardly directed toward catheter 70 as indicated at 97 in FIG. 4 due to the location of outlet 62 in the backwardly flaring portion 50 of distal edge 46 which eases entry of the contrast medium. The afore-described straight-through path for the contrast media essentially eliminates the likelihood of blockage.

As shown in FIG. 1(C), the inner surface 90 of elongate element 12 is circular in shape having a radius 92 essentially the same as that of the outer diameter of catheter 70. Inner surface 90 preferably extends over about one quarter of the periphery of catheter 70 as indicated at 94. Also, as shown in FIG. 4, the radius 95 of outer surface 96 is slightly less than that of inner surface 90 so that a slight crown is formed on the outer surface 96 and urethra 72 is thereby very slightly distended to expand the space 88 between catheter 70 and urethra 72 for initial reception of contrast medium 82.

As shown in the cross-section of FIG. 1(B) the center line 99 of through bore 62 is slightly below the central axis 34 of spacer means 36, as shown at 93 until it reaches the central axis 30 of locking member 20 due to the slight slope of the through bore 62.

There has been described and illustrated herein a device for use in connection with pericatheter retrograde urethrography in accordance with the present invention. While particular embodiments of the invention have been described, it is not intended that the invention be limited exactly thereto, as it is intended that the invention be as broad in scope as the art will permit. Thus, while the pericatheter device was described as having being made of one type of plastic, it will be appreciated that other plastics could be utilized. Also, while the mating portion of the device was described as a female luer for mating with a syringe, it will be appreciated that other mating means such as, e.g., luer locks could be utilized. Further, while the through-bore was described as being central at the distal end of the elongate element, and being off-centered at different locations of the elongate element, it will be appreciated that depending upon the exact dimensions and shapes of the elongate element, the spacer means, and the mating means, the through-bore could be centered or eccentered accordingly. What is important is that a straight path be provided from the mating means, through the spacer means, and through the elongate element such that insert molding is possible. Therefore, those skilled in the art should appreciate that other changes and modifications may be made to the invention as described in the specification without departing from the spirit and scope of the invention.

We claim:

1. Pericatheter type disposable device in the form of a unitary single component formed in one piece from substantially rigid plastic, said device being for use in a urethra having an in-dwelling catheter, and for use with a syringe means, said pericatheter type disposable device comprising:

i) an elongate element having a substantially crescent-shaped cross-section, with a smooth convex outer surface which in use contacts the inside of the urethra, and a smooth concave inner surface which in use contacts the in-dwelling catheter, said elongate element having a central axis, a distal end and a proximal end;

ii) a mating member for engaging the syringe means, said mating member having its central axis generally parallel to said central axis of said elongate element; and iii) a spacer member intermediate and coupling said proximal end of said elongate element to said mating member, said spacer member being in line with the central axis of said mating member and being off-set from said elongate element to form a protuberance at the outer surface of said elongate member;

said device having a straight relatively small diameter through-bore extending from an opening in said distal end of the elongate element, through said elongate element, through said spacer member, and into said mating member, said through-bore being in fluid communication with said syringe means.

2. A pericatheter type device according to claim 1, wherein:

said elongate element has beveled lateral edges tapering slightly toward its distal end, said distal end also being beveled so that all the edges of said elongate element are beveled.

3. A pericatheter type device according to claim 2, wherein:

said spacer member is substantially cylindrical in shape with its central axis substantially coincident with the central axis of said mating member and having a cross-section less than that of the mating member and being rounded at the portion thereof which is contiguous the proximal end of the elongate element.

4. A pericatheter type device according to claim 2, wherein:

said elongate element is tapered toward its distal end with the tapered portion extending back from its said distal end for about 30 to 50% of the length of the elongate element.

5. A pericatheter type device according to claim 3, wherein:

said elongate element is tapered toward its distal end with the tapered portion extending back from its said distal end for about 30 to 50% of the length of the elongate element.

6. A pericatheter type device according to claim 2, wherein:

the distal end of said elongate element is tapered relative to an axis parallel to said central axis with a middle portion of said elongate element extending beyond the lateral edges of the elongate element relative to said central axis.

7. A pericatheter type device according to claim 5, wherein:

the distal end of said elongate element is tapered relative to an axis parallel to said central axis with a middle portion of said elongate element extending beyond the lateral edges of the elongate element relative to said central axis.

8. A pericatheter type device according to claim 1, where said in-dwelling catheter is of known dimensions, wherein:

the inner surface of the elongate element is curved with a predetermined radius which is essentially the same as the outer radius of said in-dwelling catheter of known dimensions.

9. A pericatheter e device according to claim 3, where said in-dwelling catheter is of known dimensions, wherein:

the inner surface of the elongate element is curved with a predetermined radius which is essentially the same as the outer radius of said in-dwelling catheter of known dimensions.

10. A pericatheter type device according to claim 7, where said in-dwelling catheter is of known dimensions, wherein:

the inner surface of the elongate element is curved with a predetermined radius which is essentially the same as the outer radius of said in-dwelling catheter of known dimensions.

11. A pericatheter type device according to claim 8, wherein:

said elongate element extends over about one quarter of the periphery of said in-dwelling of known dimensions.

12. A pericatheter type device according to claim 11, wherein:

the outer surface of said elongate element is curved with a radius which is slightly smaller than the radius of said inner surface of said elongate element, thereby forming a crown.

13. A pericatheter type device according to claim 1, wherein:

the longitudinal axes of said elongate element, said spacer element, and said mating member extend substantially parallel to each other, and said pericatheter device is symmetrical about said through-bore.

* * * * *